US00PP35773P2

(12) United States Plant Patent
Olesen

(10) Patent No.: US PP35,773 P2
(45) Date of Patent: Apr. 30, 2024

(54) ROSE PLANT NAMED 'POULTY033'

(50) Latin Name: *Rosa hybrida*
Varietal Denomination: Poulty033

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 18/445,482

(22) Filed: Sep. 8, 2023

(30) Foreign Application Priority Data

Sep. 30, 2022 (QZ) ..... PBR 2022/2176

(51) Int. Cl.
*A01H 5/02* (2018.01)
*A01H 6/72* (2018.01)

(52) U.S. Cl.
USPC ..... Plt./122

(58) Field of Classification Search
USPC ..... Plt./101, 116, 122
See application file for complete search history.

*Primary Examiner* — Karen M Redden

(57) ABSTRACT

A new rose plant of the miniature class which has abundant, red flowers and attractive foliage. This new and distinct variety has shown to be uniform and stable in the resulting generations from asexual propagation.

2 Drawing Sheets

Botanical designation: *Rosa hybrida.*

Variety denomination: 'Poulty033'.

This application claims priority to Plant Breeder's Rights Application Number 2022/2176, which was filed at the Community Plant Variety Rights Office in the European Union on Sep. 26, 2022, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2015 and the resulting seeds were planted in a controlled environment in Fredensborg, Denmark. The new variety, named 'Poulty033', originated as a single seedling from the stated cross.

The new variety may be distinguished from its male pollen parent and female seed parent primarily by the following characteristics. The male pollen parent plant grows to a height of 45 cm while the new variety grows to a height of 30 cm. The female seed parent plant has red flowers with about 50 flower petals while the new variety has red flowers with about 115 petals.

The objective of the hybridization of this rose variety was to create a new and distinct variety with unique qualities, such as:

1. Uniform and abundant red flowers with long lasting quality;
2. Vigorous, but very compact growth when propagated on its own roots;
3. Exceptional disease resistance.

This combination of qualities is not present in previously available commercial cultivars of this type, known to the inventor, and distinguish 'Poulty033' from all other varieties of which we are aware.

As part of the rose development program, Mogens N. Olesen germinated the seeds from the aforementioned hybridization during winter of 2015 and conducted evaluations on the resulting seedlings in a controlled environment in Fredensborg, Denmark. 'Poulty033' was selected in the spring of 2016 by the inventor as a single plant from the progeny of the aforementioned hybridization.

Asexual reproduction of 'Poulty033' by rooted cuttings was first done by Mogens N. Olesen in the nursery in Fredensborg, Denmark in July, 2016. This initial and other subsequent asexual propagations conducted in controlled environments have demonstrated that the characteristics of 'Poulty033' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulty033'.

Specifically illustrated in FIG. 1 of the drawings are open flowers viewed from above and the side, a flower bud, flower petals detached, sepals detached showing reproductive flower parts, receptacle, and pedicel.

Figure 1:
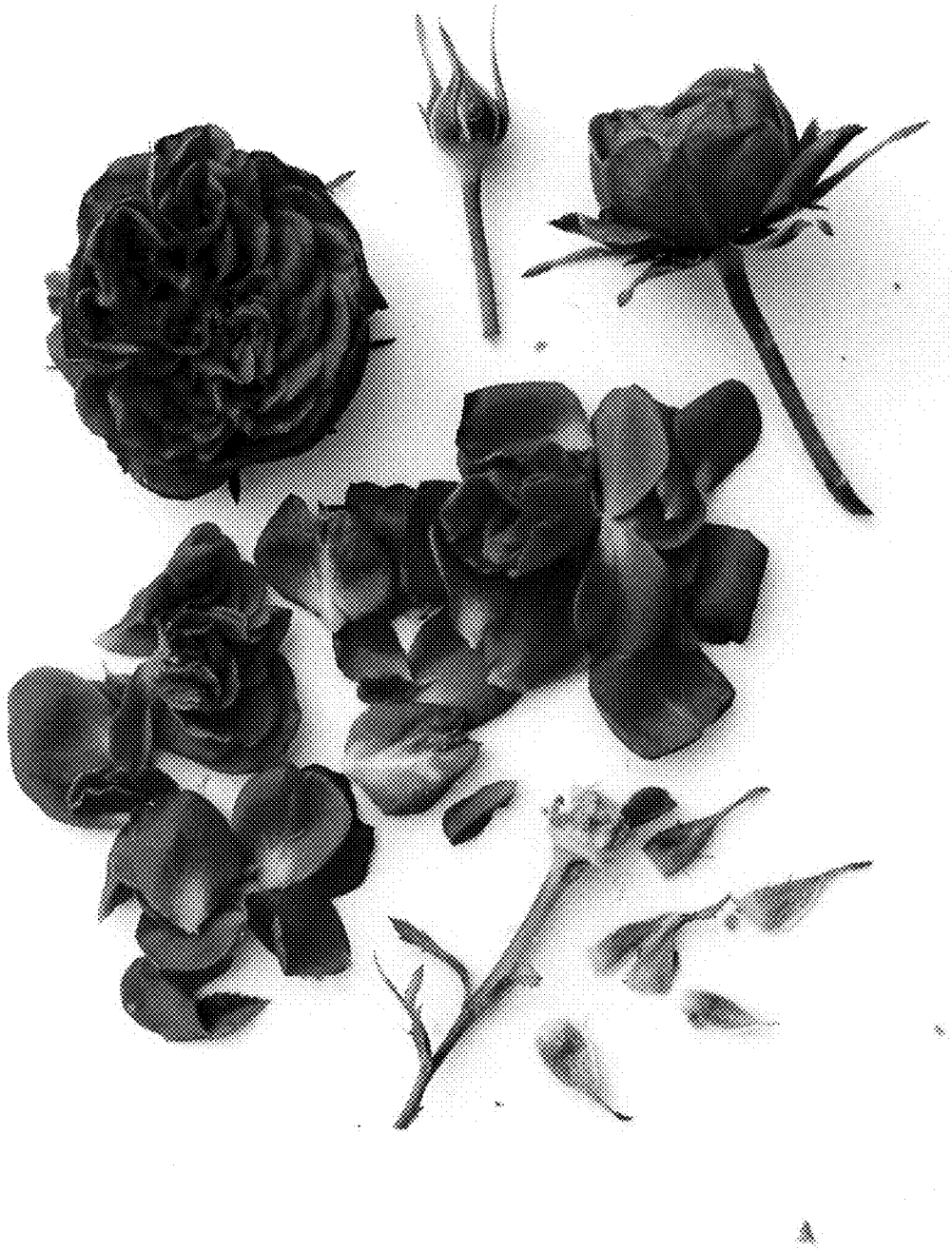
Figure 2:
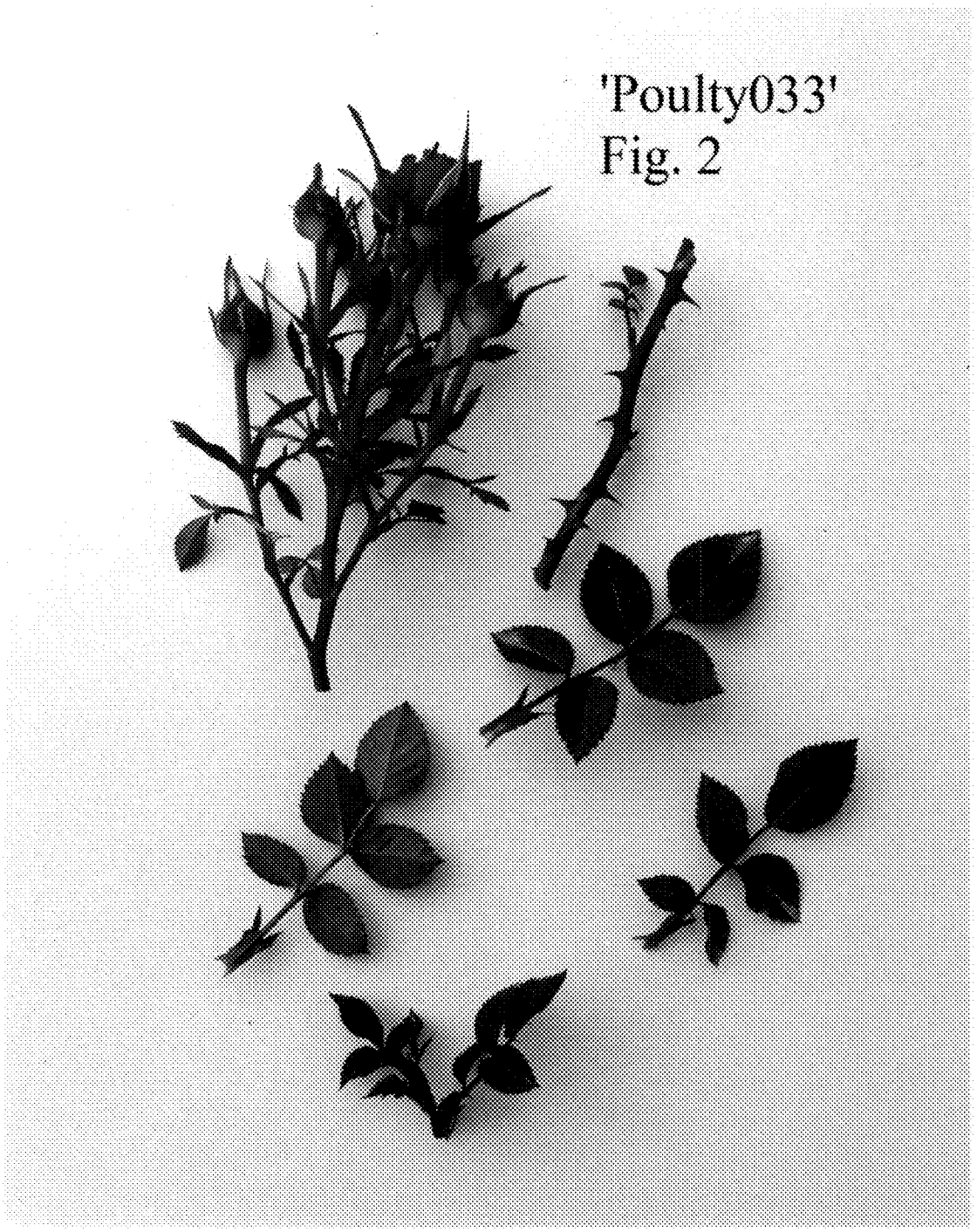

Specifically illustrated in FIG. 2 of the drawings are a cluster of flower buds on the branch, mature stem exhibiting prickles, mature leaves, and juvenile leaves. Plants shown are 1 year old.

DETAILED DESCRIPTION OF THE VARIETY

The following is a description of 'Poulty033', as observed in its growth in an outdoor nursery in Half Moon Bay California. Observed plants are 12 months of age, and were grown on their own roots in 30 cm pots. Color references are made using The Royal Horticultural Society (London, England) Colour Chart, 2001, except where common terms of color are used.

For a comparison, several physical characteristics of the rose variety 'Poulpar097', U.S. Plant Pat. No. 29,120 are compared to the claimed plant. While 'Poulty033' has 115 flower petals, 'Poulpar097' has 45 flower petals. Open flowers of 'Poulty033' are generally Red Group 53B in color while 'Poulpar097' has a general tonality of Red-Purple Group N57C. The comparison variety produces flowers in clusters of 3 to 5 flowers per branch, while the new plant produces flowers in greater quantity, about 5 to 9 flowers per branch. The claimed plant has perfumed flowers while 'Poupar097' has no scent.

FLOWER AND FLOWER BUD

Blooming habit: Continuous.

Flower bud:

*Size.*—Upon opening, 15 mm in length from base of receptacle to end of bud. Bud diameter is 10 mm.

*Bud form.*—Globose.

*Bud color.*—As sepals divide petals are Red Group 53A.

*Sepal inner surface.*—Color: Yellow-Green Group 146D with intonations of Greyed-Red Group 178A. Surface: Lightly pubescent.

*Sepal outer surface.*—Color: Yellow-Green Group 144A with intonations of Greyed-Red Group 178A. Texture: Smooth.

*Sepal shape.*—Apex: Cirrhose. Base: Flat at union with receptacle.

*Sepal margin.*—Margins have weak or absent foliaceous appendages on three of the five sepals.

*Sepal size.*—21 mm long, 9 mm wide.

*Receptacle.*—Texture: Smooth. Size: 6 mm in height, 7 mm wide. Color: Yellow-Green Group 144A with intonations of Greyed-Red Group 180A. Shape: Funnel.

*Pedicel.*—Surface: Partially rough with fragrant stipitate glands. Length: About 25 mm. Diameter: 3 mm on average. Color: Yellow-Green Group 144A & Greyed-Red Group 180A. Strength: Strong.

*Peduncle.*—Length: 2 to 5 cm. Diameter: About mm. Color: Yellow-Green Group 145A with intonations of Greyed-Red Group 180A. Texture: Smooth.

Flower bud development: Flower buds are borne in clusters of 5 to 9 flower buds per stem.

Flower bloom:

*Fragrance.*—Moderate to strong honey like perfume.

*Duration.*—The blooms have a duration on the plant of approximately 21 days. Petals fall cleanly away from plant after flowers have fully matured.

*Size.*—Flower diameter is 54 mm when open. Flower depth is 17 mm.

*Flower shape.*—Quartered-rosette, very double, with many overlapping petals packed into quarter sections.

*Shape of flower, side view.*—The upper portion is flat. The lower portion is flat.

Petalage: Under normal conditions, flowers have about 115 petals.

General tonality of flower: Open flowers are Red Group 53B.

Petal color:

*Upon opening, outer and inner petals.*—Upper surface: Red Group 53B with streaks of Red-Purple 62A at the basal zone. Other intonations at the basal and middle zone are shades of N57B. Lower surface: Red-Purple Group 60B.

*Basal petal spots, upon opening.*—Upper surface: Yellow Group 2D. Lower surface: Yellow Group 2D.

*After opening, the petal colour does not change.*

Petals:

*Petal reflex.*—Light.

*Margin.*—Entire and uniform. Moderate to strong undulations.

*Shape.*—Broad and elliptic. Apex shape: Rounded. Base shape: Acute.

*Size.*—mm (l)×mm (w).

*Texture.*—Smooth.

*Thickness.*—Average.

Petaloids:

*Size.*—38 mm (l) by 36 mm (w).

*Quantity.*—About 30.

*Shape.*—Elliptical with an acute base and rounded apex.

*Color.*—The upper surface is Red Group 53B with a basal petaloid spot of Yellow Group 2D. The lower surface is Red-Purple Group 60B with a basal petaloid spot of Yellow Group 2D.

Reproductive flower parts:

*Pollen.*—None observed.

*Anthers.*—Size: 2 mm in length. Color: Yellow Group 11A. Quantity: 58 on average.

*Filaments.*—Color: Orange Group 26B. Length: 3 mm.

*Pistils.*—Length: 7 mm. Quantity: 25 on average.

*Stigmas.*—Color: Green-White Group 157A.

*Styles.*—Color: Green-White Group 157A.

*Location of stigmas.*—Superior in location relative to the length of the filaments and the height of the anthers.

*Hips.*—None Observed.

PLANT

Plant growth: Upright and very bushy. Plants are 30 cm in height, and 40 cm wide.

Stems:

*Color of juvenile growth.*—Yellow-Green Group 144B with intonations of Greyed-Purple Group 183B.

*Color of mature growth.*—Yellow-Green Group 144A with intonations of Greyed-Purple Group 183B.

*Length.*—Canes are about 10 cm from the base of the plant to the flowering portion.

*Diameter.*—About 3.5 mm.

*Internodes.*—On mature canes about 20 mm between nodes.

*Surface texture.*—Young wood: Smooth. Older wood: Smooth.

Long prickles:

*Incidence.*—10 prickles per 10 cm of stem.

*Size.*—Average length of prickles on mature stems is 4 mm.

*Shape.*—Upper portion is linear. Lower portion is concave.

*Color.*—Juvenile prickles: Greyed-Red Group 181B. Mature prickles: Greyed-Red Group 181B.

Plant foliage:

*Compound leaf.*—83 mm (l)×50 (w).

*Quantity.*—3 leaves per 10 cm of stem on average.

*Leaf bearing angle to the stem.*—45 degrees.

*Color of juvenile foliage*.—Upper side: Yellow-Green Group 144A with marginal intonations of Greyed-Purple Group 184A. Lower side: Yellow-Green Group 144B.

*Color of mature foliage*.—Upper side: Yellow-Green Group 147A. Lower side: Yellow-Green Group 147B.

Plant leaves and leaflets:

*Stipules*.—Size: 13 mm long, 2 mm wide. Quantity: 2 per compound leaf. Shape: Linear, slightly broad based with outward extending apex. Margins: Finely serrated. Color: Yellow-Green Group 144A with some intonations of Greyed-Purple Group 183B.

*Petiole*.—Length: About 21 mm. Diameter: 2 mm. Upper surface color: Yellow-Green Group 144A with some intonations of Greyed-Purple Group 183B. Lower surface color: Yellow-Green Group 144A.

*Rachis*.—Length: About 30 mm. Upper surface color: Greyed-Purple Group 183A. Lower surface color: Yellow-Green Group 144A.

*Leaflet*.—Quantity: Normally 5 leaflets. Margins: Serrated. Size: Terminal leaflets are about 30 mm long, 20 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulty033' substantially as described and illustrated herein.

* * * * *

'Poulty033'

'Poulty033'